(12) United States Patent
Sakai

(10) Patent No.: US 10,147,209 B2
(45) Date of Patent: *Dec. 4, 2018

(54) MICROPARTICLE ANALYZING APPARATUS AND DATA DISPLAYING METHOD

(71) Applicant: Sony Corporation, Tokyo (JP)

(72) Inventor: Yoshitsugu Sakai, Kanagawa (JP)

(73) Assignee: Sony Corporation, Tokyo (JP)

( * ) Notice: Subject to any disclaimer, the term of this patent is extended or adjusted under 35 U.S.C. 154(b) by 56 days.

This patent is subject to a terminal disclaimer.

(21) Appl. No.: 15/460,493

(22) Filed: Mar. 16, 2017

(65) Prior Publication Data

US 2017/0186198 A1    Jun. 29, 2017

Related U.S. Application Data

(62) Division of application No. 13/089,569, filed on Apr. 19, 2011, now Pat. No. 9,619,907.

(30) Foreign Application Priority Data

Apr. 28, 2010  (JP) .................................. 2010-104520

(51) Int. Cl.
| | | |
|---|---|---|
| *G06T 11/00* | (2006.01) | |
| *G06T 11/20* | (2006.01) | |
| *G01N 21/64* | (2006.01) | |
| *G01N 15/14* | (2006.01) | |

(52) U.S. Cl.
CPC ........ *G06T 11/206* (2013.01); *G01N 15/1463* (2013.01); *G01N 21/645* (2013.01); *G01N 21/6428* (2013.01); *G06T 11/001* (2013.01); *G01N 2021/6421* (2013.01); *G01N 2021/6423* (2013.01); *G01N 2021/6441* (2013.01)

(58) Field of Classification Search
CPC ....... G01N 15/1463; G01N 2021/6421; G01N 2021/6423; G01N 2021/6441; G01N 21/6428; G01N 21/645; G06T 11/001; G06T 11/206
See application file for complete search history.

(56) References Cited

U.S. PATENT DOCUMENTS

| | | |
|---|---|---|
| 5,991,028 A | 11/1999 | Cabib et al. |
| 6,592,822 B1 | 7/2003 | Chandler |
| 7,280,204 B2 | 10/2007 | Robinson et al. |
| 7,625,712 B2 | 12/2009 | Paul et al. |

(Continued)

FOREIGN PATENT DOCUMENTS

| | | |
|---|---|---|
| CN | 101419171 | 4/2009 |
| JP | 61-100832 | 5/1986 |

(Continued)

OTHER PUBLICATIONS

Japanese Office Action dated Dec. 1, 2015, for corresponding Japanese Application No. 2014-161690.

(Continued)

*Primary Examiner* — Sing-Wai Wu
(74) *Attorney, Agent, or Firm* — K&L Gates LLP

(57) ABSTRACT

Disclosed herein is a microparticle analyzing apparatus including a detecting portion configured to simultaneously detect a fluorescence generated from a microparticle in plural wavelength regions and a displaying portion configured to display thereon detection results in the plural wavelength regions in a form of a spectrum.

40 Claims, 3 Drawing Sheets

(56) References Cited

U.S. PATENT DOCUMENTS

| | | |
|---|---|---|
| 2003/0108911 A1 | 6/2003 | Klimant et al. |
| 2005/0264001 A1 | 12/2005 | Kerns et al. |
| 2005/0275839 A1 | 12/2005 | Robinson et al. |
| 2008/0108146 A1 | 5/2008 | Jiang |
| 2009/0108214 A1 | 4/2009 | Shinoda et al. |
| 2010/0034105 A1 | 2/2010 | Sega et al. |

FOREIGN PATENT DOCUMENTS

| | | |
|---|---|---|
| JP | 62-034058 | 2/1987 |
| JP | 05-072113 | 3/1993 |
| JP | 06-148076 | 5/1994 |
| JP | 08-145796 | 6/1996 |
| JP | 09-509250 | 9/1997 |
| JP | 10-019780 | 1/1998 |
| JP | 2006-230333 | 9/2006 |
| JP | 2007-047492 | 2/2007 |
| JP | 2007-518106 | 7/2007 |
| JP | 2009-109933 | 11/2007 |
| JP | 2008-500558 | 1/2008 |
| JP | 2009-180706 | 2/2008 |
| JP | 2008-524601 | 7/2008 |
| JP | 2009-109218 | 5/2009 |
| JP | 2009-520990 | 5/2009 |
| JP | 2009-270990 | 11/2009 |
| WO | 2009/055427 | 4/2009 |

OTHER PUBLICATIONS

Japanese Office Action dated Jun. 2, 2015, for corresponding Japanese Application No. 2014-16190.

Chinese Office Action dated May 5, 2014, for corresponding Chinese Application No. 201110099690.7.

Japanese Office Action dated May 7, 2014, for corresponding Japanese Application No. 2010-104520.

Fundamental Principles and Practical Skills of Flow Cytometry, Zhihui, Liang, pp. 1-26 Huazhong University of Science and Technology Press, Jun. 30, 2008.

Japanese Office Action dated Oct. 21, 2014 for corresponding Japanese Application No. 2010-104520.

Japanese Office Action dated Nov. 5, 2013 for Japanese Application No. 2010-104520.

Sonja Wulff et al., "Flow Cytometry Educational Guide," 2nd Edition, Dako, 2006.

Japanese Office Action for Application No. 2017-132644 dated Jul. 24, 2018 (4 pages).

F I G . 4
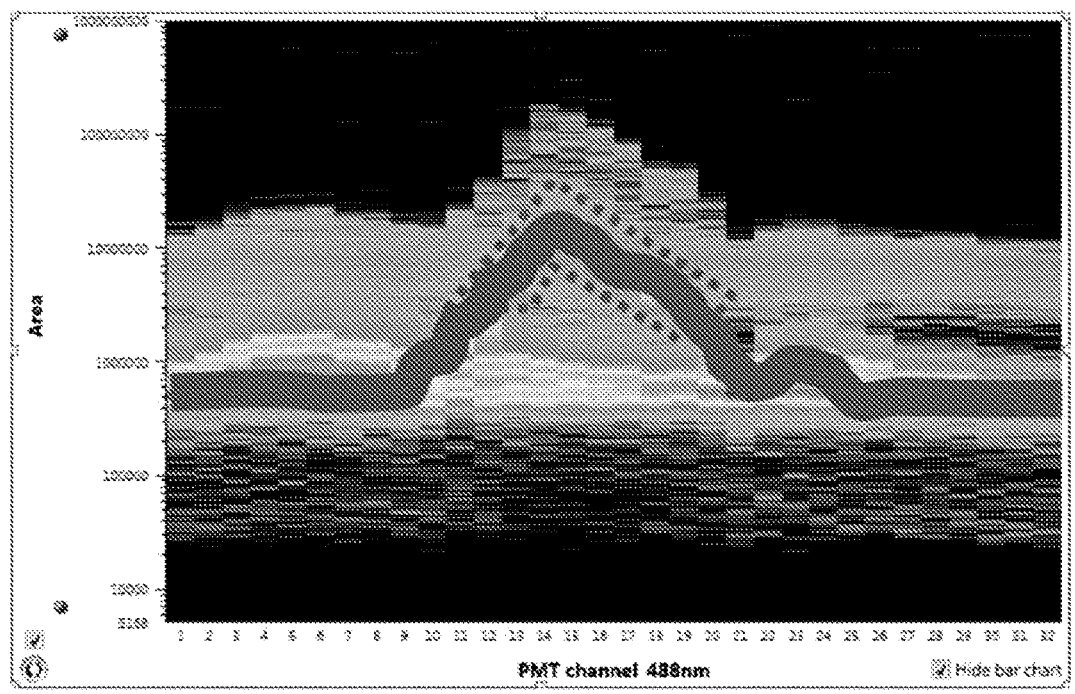

MICROPARTICLE ANALYZING APPARATUS AND DATA DISPLAYING METHOD

CROSS REFERENCES TO RELATED APPLICATIONS

The present application is a divisional of U.S. application Ser. No. 13/089,569, filed on Apr. 19, 2011, which claims priority to Japanese Priority Patent Application JP 2010-104520, filed in the Japan Patent Office on Apr. 28, 2010, the entire content of each of which is hereby incorporated by reference herein.

BACKGROUND

The present application relates to a microparticle analyzing apparatus and a method of displaying data obtained through a measurement by using the microparticle analyzing apparatus. More particularly, the application relates to a technique for detecting a light emitted from a microparticle, and analyzing a kind of light thus emitted, and the like.

In general, when a biologically-relevant microparticle such as a cell, a microbe or a liposome is analyzed, a flow cytometry (flow cytometer) is utilized. This technique, for example, is described in a non-patent literary document of "Additional Volume of Cell Engineering Experimental Protocol Series Flow Cytometry Capable of being Manipulated with Freedom," supervised by Takamitsu Nakauchi Shujunsha Co., Ltd. 2nd edition published on Aug. 31, 2006. The flow cytometry is based on a method in which a laser beam (excited light) having a specific wavelength is radiated to microparticles which are caused to flow in a line within a flow path, and fluorescences or scattered lights emitted from the microparticles are detected, thereby analyzing the plural microparticles one by one. With the flow cytometry, lights detected by respective photodetectors are converted into electrical signals to be quantified, and a statistical analysis is carried out for the resulting electrical signals thus quantified, thereby making it possible to judge kinds, sizes, structures, etc. of individual microparticles.

In addition, in recent years, in the flow cytometry, a multicolor analysis using plural fluorescent dyes has been in widespread use. This flow cytometry, for example, is described in Japanese Patent Laid-Open No. 2006-230333 and JP-T-2008-500558. Each of the existing flow cytometries normally includes plural light sources corresponding to different wavelengths, respectively, and plural detectors for detecting lights emitted from respective dyes. On the other hand, since a fluorescent dye has a spectrum, when plural fluorescent dyes are used in one measurement as with the multicolor analysis, lights from the respective fluorescent dyes other than an objective fluorescent dye are leaked to the detectors, thereby reducing the analysis precision. In order to cope with such a situation, with the existing flow cytometer, in order to extract only the optical information from the objective fluorescent dye, mathematical correction, that is, fluorescence correction is carried out when the lights detected by using the respective photodetectors are converted into the electrical signals to be quantified.

SUMMARY

As has been described, the fluorescent dyes have the spectra peculiar thereto, respectively, and the spectrum information thereof becomes important data representing the features of the fluorescent dyes themselves. However, with the existing flow cytometer, the light from the objective fluorescent dye, for example, is detected by the sensor for receiving a light having a specific bandwidth, and the data detected by the sensor is treated as corresponding data. Therefore, there is caused a problem that it may be difficult to propose the spectrum information on the fluorescent dyes.

The present application has been made in order to solve the problems described above, and it is therefore primarily desirable to provide a microparticle analyzing apparatus and a data displaying method each of which is capable of measuring spectra of fluorescences generated from microparticles, respectively, and visually understanding measured data by a user.

In order to attain the desire described above, according to an embodiment, there is provided a microparticle analyzing apparatus including: a detecting portion configured to simultaneously detect a fluorescence generated from a microparticle in plural wavelength regions; and a displaying portion configured to display thereon detection results in the plural wavelength regions in a form of a spectrum.

According to the embodiment, since it is possible to propose the spectrum information on the fluorescence generated from the microparticle, the user can visually understand the measured data irrespective of presence or absence of the fluorescence correction, and the results of the fluorescence correction. Also, for example, the data on the specific region is extracted, thereby obtaining the various kinds of pieces of information on the microparticle.

According to another embodiment, there is provided a data displaying method including the steps of: simultaneously detecting a fluorescence generated from a microparticle in plural wavelength regions; and displaying detected data for each wavelength region in a form of a spectrum.

As set forth hereinabove, according to the present application, since it is possible to propose the spectrum information on the fluorescence generated from the microparticle, the user can visually understand the measured data.

Additional features and advantages are described herein, and will be apparent from the following Detailed Description and the figures.

BRIEF DESCRIPTION OF THE FIGURES

FIG. 4 is a view showing an example of display obtained after completion of the application of the gate.

DETAILED DESCRIPTION

Figure 1:
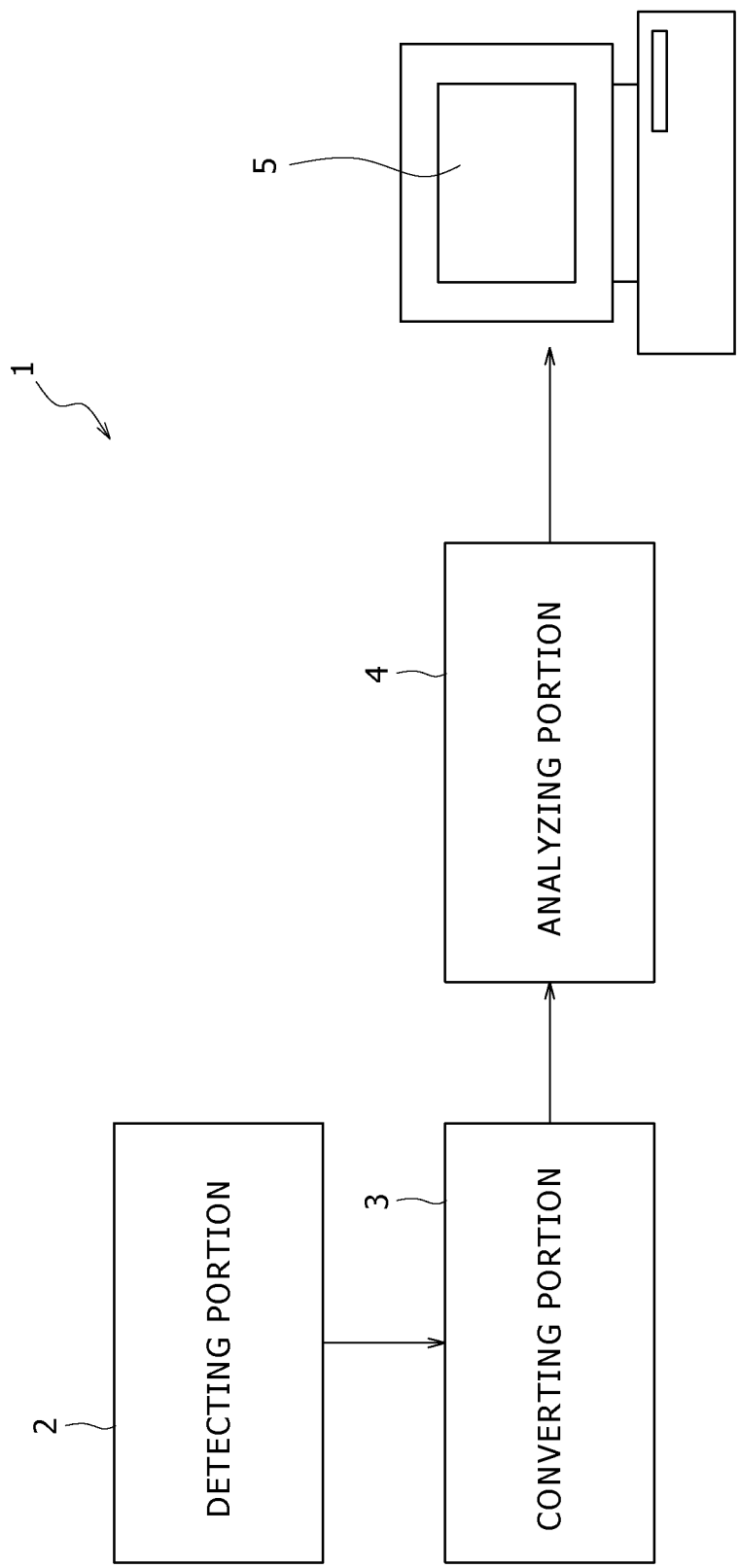
FIG. 1 is a block diagram showing a configuration of a microparticle analyzing apparatus according to a second embodiment.

Embodiments of the present application will be described below in detail with reference to the drawings.

It is noted that the present application is by no means limited to embodiments which will be described below. In addition, the description will now be given in accordance with the following order.

1. First Embodiment (A method of displaying a spectrum)
2. Second Embodiment (A microparticle analyzing apparatus for displaying a spectrum)

1. First Embodiment

Entire Constitution

Firstly, a data displaying method according to a first embodiment will be described. With the data displaying method according to the first embodiment, a fluorescence generated from a microparticle such as a cell or a microbead is simultaneously detected in plural wavelength regions, and detected data for each wavelength region is displayed in the form of a spectrum.

Detected Data

With the data displaying method of the first embodiment, a light detected by a photodetector is converted into a voltage pulse (electrical signal) every wavelength region, and the resulting voltage pulse is quantified to obtain detected data. Specifically, a height, a width and an area of the voltage pulse are obtained, thereby obtained the detected data.

Display Form

With the data displaying method of the first embodiment, the detected data, for each wavelength region, obtained by using the method described above is displayed in the form of a spectrum. Although the data displaying method is especially by no means limited, for example, a density spectrum, a dot plot, a contour line or the like is given. In addition, it is possible that only data in a specific region is extracted from the spectrum being displayed, an image of a spectrum chart is enlarged, a histogram or a two-dimensional plot is displayed, and so forth.

In addition, with the data displaying method of the first embodiment, it is also possible that the detected data which is acquired by continuously detecting plural microparticles is arithmetically operated, and results of the arithmetical operation are displayed. With regard to the arithmetic operation, for example, there are given an accumulation of the detected data, a calculation of an average value of the detected data on all the microparticles, and the like. Moreover, with the data displaying method of the first embodiment, although the display can be carried out while the detection is carried out, the detected data may be temporarily preserved, and the data thus preserved may be read out and displayed. In this case as well, the detected data may be arithmetically operated and results of the arithmetical operation may be displayed.

With the existing two-dimensional plot, even when the fluorescence correction is carried out, it is difficult for a user to visually judge the data obtained through the fluorescence correction. On the other hand, with the data displaying method of the first embodiment, since it is possible to propose the spectrum information on the fluorescence generated from the microparticle, the user can visually understand the measured data irrespective of presence or absence of the fluorescence correction, and the results of the fluorescence correction. Also, with the data displaying method of the first embodiment, the data in the specific region is extracted, thereby making it possible to obtain the various kinds of pieces of information on the microparticle.

The data displaying method of the first embodiment is by no means limited to application to an analyzing apparatus for the microparticle, the cell or the like. For example, the data displaying method of the first embodiment can also be applied to manufacturing equipment, inspection equipment, medical equipment, or the like.

2. Second Embodiment

Entire Configuration of Apparatus

Figure 2:
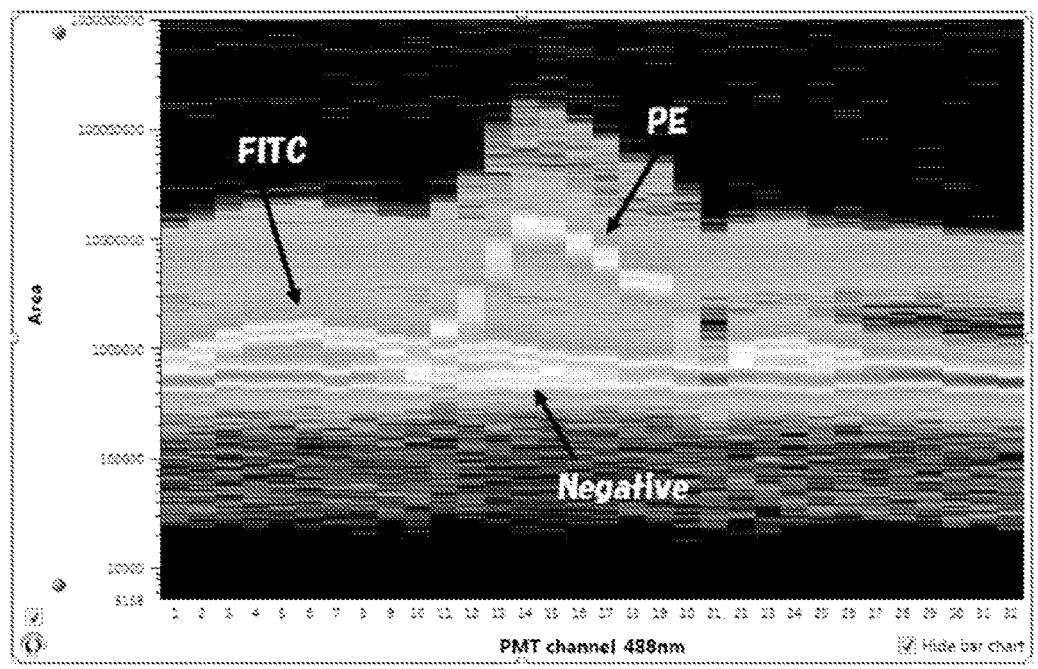
FIG. 2 is a view showing an example of display of measurement results.

Next, a microparticle analyzing apparatus according to a second embodiment will be described. FIG. 1 is a block diagram showing a configuration of the microparticle analyzing apparatus according to the second embodiment. Also, FIG. 2 is a view showing an example of display of measurement results obtained from the microparticle analyzing apparatus of the second embodiment. As shown in FIG. 1, the microparticle analyzing apparatus 1 is provided with at least a detecting portion 2, a converting portion 3, an analyzing portion 4, and a displaying portion 5.

Configuration of Detecting Portion 2

All it takes is that the detecting portion 2 has a configuration with which a fluorescence generated from a microparticle as an object of an analysis can be simultaneously detected in plural wavelength regions. Specifically, the detecting portion 2 can have a configuration in which sensors capable of detecting wavelength regions are disposed so as to correspond to the wavelength regions, respectively, or a configuration including a detector capable of simultaneously detecting plural lights as with a multichannel Photo-Multiplier Tube (PMT) or the like. All it takes is that the number of wavelength regions detected by the detecting portion 2, that is, the number of channels of the detector disposed in the detecting portion 2 or the number of sensors disposed in the detecting portion 2 is equal to or larger than the number of dyes used. In this case, preferably, the number of channels of the detector disposed in the detecting portion 2 or the number of sensors disposed in the detecting portion 2 is equal to or larger than twelve because in the current multicolor analysis, six to eight colors are general, and ten to twelve colors are used at the most.

In addition, the microparticle analyzing apparatus 1 of the second embodiment may also adopt such a construction that a spectroscope is provided in the detector 2, and after the fluorescence generated from the microparticle is spectrally diffracted in the spectroscope, the fluorescence thus spectrally diffracted is made incident to the detector such as the multichannel PMT. Moreover, an objective lens, a condensing lens, a pin hole, a band-cut filter, a dichroic mirror, or the like can also be provided as may be necessary.

Configuration of Converting Portion 3

The converting portion 3 operates to convert the lights, in the respective wavelength regions, detected by the detecting portion 2 into voltage pulses (electrical signals), respectively. For example, an AD converter or the like can be used as the converting portion 3.

Configuration of Analyzing Portion 4

With the analyzing portion 4, the voltage pulses obtained through the AD conversion in the converting portion 3 are processed by using an electronic computer or the like to quantify the voltage pulses, thereby obtaining the detected data. Specifically, a height (peak), a width or an area (integral) of the voltage pulse is obtained, and is used as the detected data. Also, the results are associated with the wavelength regions, respectively, and are preserved in a memory portion (not shown) or the like.

Configuration of Displaying Portion 5

The displaying portion 5 operates to display thereon the detected data obtained in the processing in the analyzing portion 4, that is, the measurement results obtained from the microparticle analyzing apparatus 1 of the second embodiment. Specifically, for example, as shown in FIG. 2, "a density plot" representing a fluorescence intensity for each channel, or the like is displayed on the displaying portion 5. In FIG. 2, an axis of abscissa represents a channel number of the detecting portion 2, and an axis of ordinate represents an intensity. When the detected wavelength is made short as the channel number becomes larger, the spectrum information on the detected light (fluorescence) is obtained.

Operation of Microparticle Analyzing Apparatus 1

Next, an operation of the microparticle analyzing apparatus 1 of the second embodiment will be described. Although the microparticle analyzed by using the microparticle analyzing apparatus 1 is especially by no means limited, for example, the cell, the microbead or the like is given. In addition, the kinds and the number of fluorescent dyes modifying such microparticles are also especially by no means limited. Thus, the known dyes such as fluorescein isothiocyanate ($C_{21}H_{11}NO_5S$: FITC), phycoerythrin (PE), peridinin chlorophyll protein (PerCP), PE-Cy5 and PE-Cy7 can be suitably selected and used as may be necessary. In addition, each of the microparticles may be modified with plural fluorescent dyes.

When the microparticle is intended to be optically analyzed by using the microparticle analyzing apparatus 1, firstly, an excited light is emitted from a light source of a light radiating portion to be radiated to the microparticle which is being caused to pass within the flow path. Secondary, a fluorescence generated from the microparticle is detected in the detecting portion 2. In this case, for example, the fluorescence generated from the microparticle is spectrally diffracted in a spectroscope such as a prism or a diffraction grating, whereby the resulting lights having different wavelength regions, respectively, are made incident to the sensors or the channels of the PMT disposed in the detecting portion 2.

After that, the data, in the wavelength regions, acquired in the detecting portion 2 is converted into voltage pulses in the converting portion 3, and the resulting voltage pulses are quantified in the analyzing portion 4 to be preserved therein. The results of the analysis, for example, are displayed in the form of "the density plot" shown in FIG. 2, or the like on the displaying portion 5. It is noted that "the density plot" shown in FIG. 2 is the results obtained by measuring a sample obtained by mixing a sample modified with only FITC, a sample modified with only PE, and a Negative sample with one another by using a 32-channel PMT.

For "the density plot," a channel number (wavelength-dependent number) of the PMT is plotted on an axis of abscissa, and a fluorescence intensity is plotted on an axis of ordinate. In this case, the number, 0, of accumulation is set as blue, and red comes to be obtained as the number of accumulation is increased, that is, the density is increased. At this time, when the number of the channel corresponding to the shortest detected wavelength is set as 1, and the detected wavelength becomes short as the number of the channel becomes larger, information corresponding to the fluorescence spectrum is obtained. Also, from the spectrum information, the user can recognize what kind of fluorescence the sample is labeled with.

Figure 3:
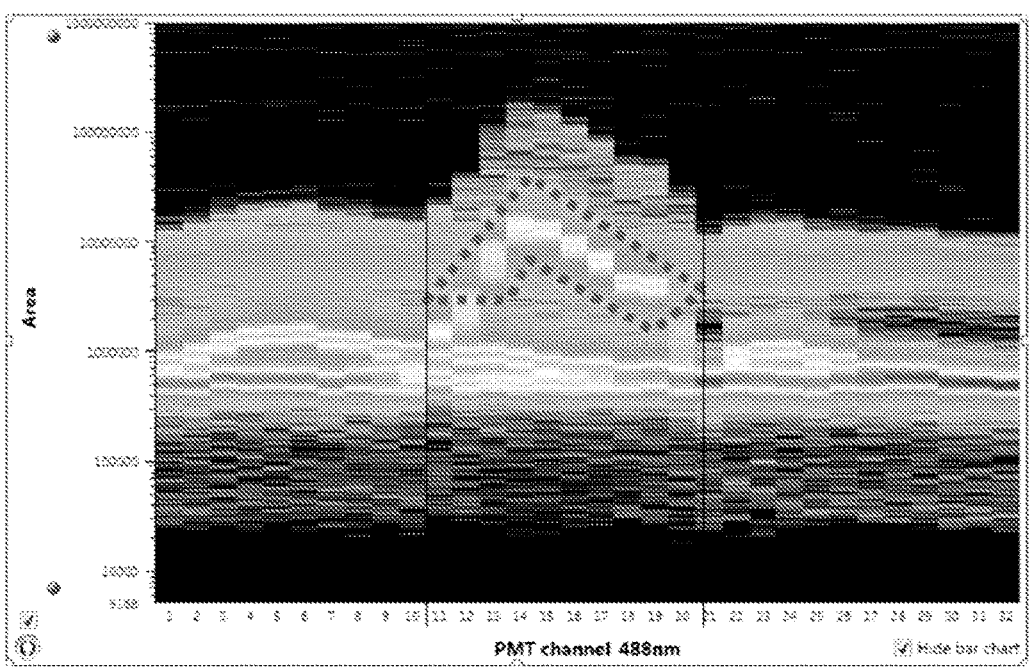
FIG. 3 is a view showing a method of applying gate to the example of the display of the measurement results shown in FIG. 2.

In addition, with the microparticle analyzing apparatus 1 of the second embodiment, it is also possible to carry out the gating for selecting only the specific sample group with respect to the data shown in FIG. 2, and extracting and displaying the data on only the specific sample group (microparticles). The display form in this case is especially by no means limited, and thus the data concerned can be displayed in the form of various kinds of forms such as a histogram, a two-dimensional plot and a spectrum chart. FIG. 3 is a view showing a method of applying the gate to the example of the display shown in FIG. 2, and FIG. 4 is a view showing an example of display after completion of the application of the gate. Since in the existing flow cytometer, normally, the gating processing is executed for the two-dimensional plot, the gate is applied to only the information for two channels.

On the other hand, as shown in FIG. 3, in the microparticle analyzing apparatus 1 of the second embodiment, the gate, for example, is applied with ten channels as a batch with respect to the fluorescence spectrum. Also, as shown in FIG. 4, for the data on the sample to which the gating is applied, a dot-plot mode can be adopted in the spectrum plot, or a color can be changed in the spectrum plot. As a result, it is possible to realize the more explicit gating, and thus the user can clearly confirm the data concerned. In addition, the data on the sample to which the gating is applied can also be displayed in the form of a two-dimensional plot.

In addition, the region to which the gating is to be applied can be selected based on the fluorescence spectrum. Therefore, for example, whether or not two kinds of fluorescent dyes are fixed to one microparticle, or whether or not two microparticles modified with different fluorescent dyes, respectively, are contained can be easily sheared. In addition, the gating is applied to a portion to which no fluorescence is leaked from any other fluorescent dyes, whereby the user can visually get the various kinds of pieces of information from the data being displayed irrespective of presence or absence of the fluorescence correction or the results of the fluorescence correction.

It should be noted that with the microparticle analyzing apparatus 1 of the second embodiment, not only "the density plot" or "the dot plot" described above, but also "a contour line plot," "a two-dimensional plot," "a two-dimensional histogram" or the like can be displayed. In addition, the characteristics of plural microparticles can be continuously measured, and the data detected in the detecting portion 2 is accumulated at any time and can be reflected in the fluorescence spectrum being displayed on the displaying portion 5 at real time. Moreover, the data preserved can be read out and displayed, and the results of continuously measuring the characteristics of plural microparticles can be temporarily preserved and can be displayed by using an average value of all the samples.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A microparticle analyzing apparatus, comprising:
   a detector configured to simultaneously detect a fluorescence generated from a plurality of microparticles in plural wavelength regions; and
   a display configured to display thereon detected data in each one of the plural wavelength regions,
   wherein the detected data in each one of the plural wavelength regions has a plurality of colors, and a respective color at each fluorescence intensity in each wavelength region indicates an accumulated number of microparticles at said fluorescence intensity in said wavelength region,
   wherein the detected data is based on a same wavelength region and a same fluorescence intensity and is mapped for each one of the plural wavelength regions and each fluorescence intensity, and
   wherein the display is configured to display gate information.

2. The microparticle analyzing apparatus according to claim 1, wherein the gate information is associated with a gated area of the detected data.

3. The microparticle analyzing apparatus according to claim 1, wherein the gate information includes an indicator indicating a gating range.

4. The microparticle analyzing apparatus according to claim 3, wherein the indicator is associated with a histogram.

5. The microparticle analyzing apparatus according to claim 3, wherein the indicator is associated with a two-dimensional plot.

6. The microparticle analyzing apparatus according to claim 3, wherein the indicator is associated with a spectrum chart.

7. The microparticle analyzing apparatus according to claim 1, wherein the display is configured to display a histogram of a gated area of the detected data.

8. The microparticle analyzing apparatus according to claim 1, wherein the display is configured to display a two-dimensional plot of a gated area of the detected data.

9. The microparticle analyzing apparatus according to claim 1, wherein the display is configured to display a spectrum chart of a gated area of the detected data.

10. The microparticle analyzing apparatus according to claim 1, wherein the detector includes a multichannel photodetector.

11. The microparticle analyzing apparatus according to claim 1, further comprising a memory configured to store detection results obtained by the detector.

12. The microparticle analyzing apparatus according to claim 1, wherein the microparticles are configured to be modified with at least one kind of fluorescent dyes.

13. The microparticle analyzing apparatus according to claim 1, wherein the microparticles is not dyed by a fluorescent dye.

14. The microparticle analyzing apparatus according to claim 1, wherein the respective color indicates a density of microparticles at each fluorescence intensity in each wavelength region.

15. A method, comprising:
    simultaneously detecting a fluorescence generated from a plurality of microparticles in plural wavelength regions; and
    displaying detected data in each one of the plural wavelength regions,
    wherein the detected data in each one of the plural wavelength regions has a plurality of colors, and a respective color at each fluorescence intensity in each wavelength region indicates an accumulated number of microparticles at said fluorescence intensity in said wavelength region,
    wherein the detected data is based on a same wavelength region and a same fluorescence intensity and is mapped for each one of the plural wavelength regions and each fluorescence intensity, and
    wherein the display is configured to display gate information.

16. The method according to claim 15, wherein the gate information is associated with a gated area of the detected data.

17. The method according to claim 15, wherein the gate information includes an indicator indicating a gating range.

18. The method according to claim 17, wherein the indicator is associated with a histogram.

19. The method according to claim 17, wherein the indicator is associated with a two-dimensional plot.

20. The method according to claim 17, wherein the indicator is associated with a spectrum chart.

21. The method according to claim 15, wherein the display is configured to display a histogram of a gated area of the detected data.

22. The method according to claim 15, wherein the display is configured to display a two-dimensional plot of a gated area of the detected data.

23. The method according to claim 15, wherein the display is configured to display a spectrum chart of a gated area of the detected data.

24. The method according to claim 15, wherein the detector includes a multichannel photodetector.

25. The method according to claim 15, wherein a height, a width or an area of a voltage pulse obtained by converting a detected light is used as the detected data.

26. The method according to claim 15, wherein the detected data is displayed in a density plot, a dot plot or a contour line plot.

27. The method according to claim 15, wherein the microparticles are configured to be modified with at least one kind of fluorescent dyes.

28. The method according to claim 15, wherein the microparticles is not dyed by a fluorescent dye.

29. The method according to claim 15, wherein the respective color indicates a density of microparticles at each fluorescence intensity in each wavelength region.

30. A microparticle analyzing system, comprising:
    a processor,
    a detector configured to simultaneously detect a fluorescence generated from a plurality of microparticles in plural wavelength regions; and
    a display configured to display thereon detected data in each one of the plural wavelength regions,
    wherein the detected data in each one of the plural wavelength regions has a plurality of colors, and a respective color at each fluorescence intensity in each wavelength region indicates an accumulated number of microparticles at said fluorescence intensity in said wavelength region,
    wherein the detected data is based on a same wavelength region and a same fluorescence intensity and is mapped for each one of the plural wavelength regions and each fluorescence intensity, and
    wherein the display is configured to display gate information.

31. The microparticle analyzing system according to claim 30, wherein the gate information includes an indicator indicating a gating range.

32. The microparticle analyzing system according to claim 31, wherein the indicator is associated with a histogram.

33. The microparticle analyzing system according to claim 31, wherein the indicator is associated with a two-dimensional plot.

34. The microparticle analyzing system according to claim 31, wherein the indicator is associated with a spectrum chart.

35. The microparticle analyzing system according to claim 30, wherein the display is configured to display a histogram of a gated area of the detected data.

36. The microparticle analyzing system according to claim 30, wherein the display is configured to display a two-dimensional plot of a gated area of the detected data.

37. The microparticle analyzing system according to claim 30, wherein the display is configured to display a spectrum chart of a gated area of the detected data.

38. The microparticle analyzing system according to claim 30, wherein the microparticles are configured to be modified with at least one kind of fluorescent dyes.

39. The microparticle analyzing system according to claim 30, wherein the microparticles is not dyed by a fluorescent dye.

40. The microparticle analyzing system according to claim 30, wherein the respective color indicates a density of microparticles at each fluorescence intensity in each wavelength region.

* * * * *